United States Patent [19]

Granger et al.

[11] Patent Number: 5,716,627
[45] Date of Patent: Feb. 10, 1998

[54] SKIN CARE COMPOSITIONS CONTAINING FATTY ACID AMIDES, AZOLES, AND RETINOL OR RETINYL ESTER

[75] Inventors: Stewart Paton Granger, Paramus, N.J.; Anthony Vincent Rawlings, Warrington, England; Ian Richard Scott, Allendale, N.J.

[73] Assignee: Elizabeth Arden Co., Division of Conopco, Inc., New York, N.Y.

[21] Appl. No.: 638,074

[22] Filed: Apr. 25, 1996

[51] Int. Cl.$^6$ ..................................... A61K 7/48
[52] U.S. Cl. .................. 424/401; 514/844; 514/845; 514/846; 514/847
[58] Field of Search ............. 424/401; 514/844–847

[56] References Cited

U.S. PATENT DOCUMENTS

| | | | |
|---|---|---|---|
| 4,363,815 | 12/1982 | Yu et al. | 424/276 |
| 4,380,549 | 4/1983 | Van Scott et al. | 424/317 |
| 4,867,971 | 9/1989 | Ryan et al. | 424/81 |
| 5,057,501 | 10/1991 | Thornfeldt | 514/53 |
| 5,216,148 | 6/1993 | Klaus et al. | 540/517 |
| 5,308,551 | 5/1994 | Beauquey et al. | 252/548 |
| 5,348,736 | 9/1994 | Patel et al. | 424/70 |
| 5,476,852 | 12/1995 | Cauwenbergh | 514/252 |

FOREIGN PATENT DOCUMENTS

| | | |
|---|---|---|
| 2101101 | 2/1994 | Canada . |
| 0 156 508 | 10/1986 | European Pat. Off. . |
| 0 347 199 | 12/1989 | European Pat. Off. . |
| 0 388 275 | 9/1990 | European Pat. Off. . |
| 0 582 458 | 2/1994 | European Pat. Off. . |
| 0 371 559 | 10/1994 | European Pat. Off. . |
| 1126289 | 9/1968 | United Kingdom . |
| 93/19743 | 10/1993 | WIPO . |
| 93/25177 | 12/1993 | WIPO . |
| 94/03156 | 2/1994 | WIPO . |
| 95/05852 | 3/1995 | WIPO . |
| 95/17175 | 6/1995 | WIPO . |

OTHER PUBLICATIONS

Vahlquist, A. et al., "Isotretinoin Treatment of Severe Acne Affects the Endogenous Concentration of Vitamin A in Sebaceous Glands", *J. Invest. Dermatol.*,vol. 94, (1990), pp. 496–498.

Ellis, C. N. et al., "Treatment of Actinically Aged Skin with Topical Tretinoin", *Pharmacology of Retinols in Skin*, vol. 3, (1989), pp. 249–252.

Lowe, N. J. et al., "Systemic Reinoids in Psoriasis: Comparative Efficacy and Toxicity", *Pharmacology of Retinols in Skin*, vol. 3, (1989), pp. 240–248.

Abstract of WO 94/03156.
Abstract of EP 0 388 275.
Abstract of EP 0 559 304.

*Primary Examiner*—Jyothsan Venkat
*Attorney, Agent, or Firm*—Rimma Mitelman

[57] ABSTRACT

Fatty acid amides in combination with azoles and either retinol or retinyl ester resulted in a synergistic enhancement in keratinocyte proliferation and synergistic inhibition of keratinocyte differentiation. The effects of the retinol or retinyl esters in combination with fatty acid amides and azoles were analogous to treatment with retinoic acid.

2 Claims, No Drawings

SKIN CARE COMPOSITIONS CONTAINING FATTY ACID AMIDES, AZOLES, AND RETINOL OR RETINYL ESTER

FIELD OF THE INVENTION

Background of the Invention

Retinol (vitamin A) is an endogenous compound which occurs naturally in the human body and is essential for normal epithelial cell differentiation. Natural and synthetic vitamin A derivatives have been used extensively in the treatment of a variety of skin disorders and have been used as skin repair or renewal agents. Retinoic acid has been employed to treat a variety skin conditions, e.g., acne, wrinkles, psoriasis, age spots and discoloration. See e.g., Vahlquist, A. et al., *J. Invest. Dermatol.*, Vol. 94, Holland D. B. and Cunliffe, W. J. (1990), pp. 496–498; Ellis, C. N. et al., "Pharmacology of Retinols in Skin", Vasel, Karger, Vol. 3, (1989), pp. 249–252; Lowe, N. J. et al., "Pharmacology of Retinols in Skin", Vol. 3, (1989), pp. 240–248; PCT Patent Application No. WO 93/19743. Retinol and retinyl esters, such as retinyl acetate and retinyl palmitate, are easier to formulate/stabilize than retinoic acid. Unfortunately, retinol and retinyl esters are less effective than retinoic acid at providing skin benefits. The present invention is based, in part, on the discovery that certain combinations of retinol or retinyl esters with fatty acid amides and azoles result in a synergistic improvement in keratinocyte proliferation and differentiation. The effects of combination of a fatty acid amide with azole and either retinol or a retinyl ester were analogous to the effects of retinoic acid. This effect was not only greater than the effect of either retinol/retinyl ester with a fatty acid amide or of retinol/retinyl ester with azole but the three ingredients acted in synergy with each other to promote a retinoic acid response. Thus, a mixture of fatty acid amides with retinol or retinyl esters mimics retinoic acid yet is easier to use than retinoic acid.

Thornfeldt (U.S. Pat. No. 5,057,501) discloses a method for treatment of papulosquamous and eczematous diseases with a composition containing a sesquiterpene compound and from about 0.025% to about 35% of a monocarboxylic fatty acid, ester, or amide. The compositions may also include a retinoid; Thornfeldt teaches that certain retinoids, namely isotretinoin, tretinoin, errerin (all of which are stereoforms of retinoic acid) and etretinate (an ester of trimethoxyphenyl retinoic acid) have proven efficacy against papulosquamous diseases. PCT Application WO/9325177 (Procter and Gamble) discloses compositions for topical application to skin which contain a specific type of acyclic carboxamide coolant and may include retinoids such as retinoic acid and its derivatives (e.g., cis and trans). PCT application WO/9403156 (Rhone Poulenc) discloses a topical composition containing linoleic acid or a derivative as an active ingredient for treatment and prophylaxis of impure skin (e.g., skin affected by pimples, pustules, or comedones); the composition may also contain 0.025–0.1 wt. % of tretinoin. European Patent Application No. 0 388 275 (Pierre Fabre Cosmetique) discloses compositions for treating seborrhea containing alkyl carboxamide and a zinc salt which may be zinc retinoate.

Klaus et al. (U.S. Pat. No. 5,216,148) disclose the use of specific complex carboxamides for treating and preventing neoplasms, dermatoses, and aging of skin. Van Scott et al. (U.S. Pat. No. 4,380,549) and Yu et al., (U.S. Pat. No. 4,363,815) disclose treatment of acne, dry, flaky, scaly skin with a hydroxyacid or the amide thereof. EP 582,458 discloses use of N,N-(1,4C alkyl) lauramide EP 559,304 disclose the use of an amide containing a hydrocarbyl chain of at least 25 carbon atoms as a skin smoothening agent. Beauquey et al. (U.S. Pat. No. 5,308,551) disclose a skin washing and conditioning composition containing, among other ingredients, a 1–4C alkanolamide of a 8–16C fatty acid. Great Britain Patent Specification No. 1,126,289 (Hoffman-La Roche) discloses a stock vitamin preparation containing vitamin A alcohol or a vitamin A ester, an emulsifier and a solvent which is selected from an alcohol or a dialkyl amide of a monocarboxylic acid (e.g., N,N-diethylacetamide, N,N-dimethyl acetamide or N,N-dimethyl formamide). None of the above-cited documents, however mentions azoles.

Compositions containing retinoids and azoles nave been described. See for instance Yusuf et al., CA 2,101,101, Cauwenbergh, U.S. Pat. No. 5,476,852 and Keyhani, PCT Patent application WO 9505852. These documents, however, do not mention fatty acid amides.

Compositions containing azoles and fatty acid amides are also known. These compositions, however, do not include any retinoids. See for instance, WO 95/17175; EP 0 347,199; U.S. Pat. No. 4,867,971; and U.S. Pat. No. 5,348,736.

The art cited above does not disclose skin conditioning compositions based on synergistic combinations of three ingredients: a fatty acid amide, an azole and retinol or a retinyl ester. None of the art cited above addresses the need for an effective alternative to retinoic acid.

SUMMARY OF THE INVENTION

The present invention includes, in part, a skin conditioning composition containing:

(a) from about 0.001% to about 10% of retinol or a retinyl ester;

(b) from about 0.0001% to about 50% of an azole;

(c) from about 0.0001% to about 50% of a fatty acid amide wherein the fatty acid contains at least 6 carbon atoms; and (d) a cosmetically acceptable vehicle.

The term "conditioning" as used herein means prevention and treatment of dry skin, photodamaged skin, appearance of wrinkles, age spots, aged skin, increasing stratum corneum flexibility, and generally increasing the quality of skin. The composition may be used to improve skin desquamation and epidermal differentiation.

The presence of the fatty acid amide and an azole in the inventive product substantially improves the performance of retinol or a retinyl ester, i.e., fatty acid amide in combination with azole substantially increases the ability of retinol or a retinyl ester to affect cellular proliferation and differentiation. The fatty acid amide or an azole has no or little effect on improving skin benefit when used alone; a substantial increase in skin benefit is only realized when the amide and the azole are combined with retinol or a retinyl ester. In short, the present invention is based, at least in part, on the discovery of synergistic interaction between retinol or a retinyl ester, fatty acid amides, and azoles.

In a preferred embodiment of the invention, the amide is an amide of $C_8$–$C_{24}$ fatty acid, most preferably a mono- or di-alkanolamide of a $C_8$–$C_{24}$ fatty acid and the azole is climbazole.

According to the present invention, by virtue of including an effective amount of a fatty acid amide and an azole into compositions containing retinol or a retinyl ester, the performance of the compositions is substantially improved. Alternatively, lower levels of retinol or a retinyl ester may be included in the composition containing the fatty acid amide and the azole to equal the performance of a similar formulation without the amide and the azole.

DESCRIPTION OF THE PREFERRED EMBODIMENT

The inventive compositions contain, as a first essential ingredient, a compound selected from the group consisting of retinol or a retinyl ester. The term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate, retinyl lactate, retinyl glycolate, retinyl hydroxy caprylate, retinyl hydroxy laurate, retinyl tartarate.

The preferred ester for use in the present invention is selected from retinyl palmitate, retinyl acetate and retinyl propionate, because these are the most commercially available and therefore the cheapest.

Retinol or retinyl ester is employed in the inventive composition in an amount of from about 0.001% to about 10%, preferably in an amount of from about 0.01% to about 1%, most preferably in an amount of from about 0.01% to about 0.5%.

The second essential ingredient of the inventive composition is a fatty acid amide. Preferably, the fatty acid amide contains at least 6 carbon atoms. Suitable fatty acids include saturated and unsaturated, straight or branched fatty acids. Suitable fatty acids preferably contain from 8 to 24 carbon atoms, preferably from 12 to 20 carbon atoms, and most preferably from 12 to 18 carbon atoms, because longer chain fatty acid amides are more beneficial for conditioning of the skin. In the most preferred embodiment of the invention, amides of essential fatty acids are employed because essential fatty acids provide nutrition for the skin. Examples of essential fatty acids include but are not limited to linoleic, linolenic, arachidonic, gamma-linolenic, homo-gamma-linolenic, and mixtures thereof. Linoleic acid is most preferred because it is also a precursor to ceramide.

Amides suitable for use in the present invention may be simple amides (i.e., those containing a —$CONH_2$ group), N-alkyl amides, N,N-dialkyl amides, mono-alkanol amides, and di-alkanol amides. Suitable alkyl or alkanol groups contain from 1 to 30 carbon atoms, preferably from 1 to 20 carbon atoms, and most preferably from 1 to 8 carbon atoms. The preferred amides included in the present invention are mono- and di-alkanol amides, particularly of essential fatty acids. Alkanol amides are more commonly available than alkyl amides.

The preferred fatty acid amides are selected from mono- and diethanolamides of linoleic acid, palmitic acid, and coconut oil.

The amide is included in the inventive compositions in an amount ranging from about 0.0001% to about 50%, preferably from about 0.01% to about 10%, most preferably from about 0.1% to about 5%.

The third essential ingredient of the inventive compositions is an azole. Suitable azoles have Formula I.

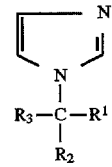

where $R_1$, $R_2$ and $R_3$ are—H or ethonyl, thioyls, alkyl containing 1–12 carbon atoms, aryl group, awl group containing 1–5 halogen atoms, heterocyclic group containing nitrogen and/or oxygen atoms and mixtures thereof.

Climbazole, miconazole, bifonazole, econazole, clotrimazole are most preferred. Also suitable for use in the present invention are 1,2,4-triazole, octyl triazole, ketoconazole, itraconazole, fluconazole, terconazole, sulconazole, liarazole, butoconazole and mixtures thereof.

The azole is included in the inventive composition in the amount of from about 0.0001% to 50%, preferably from about 0.001% to about 10%, most preferably from about 0.1% to 5%.

Cosmetically Acceptable Vehicle

The composition according to the invention also comprises a cosmetically acceptable vehicle to act as a dilutant, dispersant or carrier for the active components in the composition, so as to facilitate their distribution when the composition is applied to the skin.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the emulsion, and can, in the absence of other cosmetic adjuncts, form the balance of the composition.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be present in cosmetic compositions of the present invention. Various types of active ingredients may be present in cosmetic compositions of the present invention. Actives are defined as skin benefit agents other than emollients and other than ingredients that merely improve the physical characteristics of the composition. Although not limited to this category, general examples include sunscreens and tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Another preferred optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo-γ-linolenic acid, columbinic acid, eicosa-(n-6,9,13)-trienoic acid, arachidonic acid, γ-linolenic acid, timnodonic acid, hexaenoic acid and mixtures thereof.

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers, perfumes and preservatives (e.g., imidazolidinyl urea, dimethyl imidazolidinone and diazolidinyl urea). Amounts of these materials may range anywhere from 0.001% up to 20% by weight of the composition.

Use of the Composition

The composition according to the invention is intended primarily as a product for topical application to human skin, especially as an agent for conditioning and smoothening the skin, and preventing or reducing the appearance of wrinkled or aged skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin treatment composition of the invention can be formulated as a lotion having a viscosity of from 4,000 to 10,000 mPas, a fluid cream having a viscosity of from 10,000 to 20,000 mPas or a cream or a gel having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

MATERIALS AND METHODS

Cell Culture:

Human keratinocytes, isolated from neonatal foreskin by trypsin treatment were grown in Dulbecco Modification Eagle (DME) Hams F12 (1:1) medium/10% fetal calf serum in the presence of irradiated 3T3 mouse fibroblasts for establishing dividing keratinocyte colonies. Cells were grown under the above condition until their second passage and kept frozen for future use. Frozen second passage keratinocytes were thawed and plated into the above medium and grown for five days before they were switched to a serum-free MCDB 153-based medium keratinocyte growth medium (KGM) from Clonetics Corporation, San Diego, Calif., containing 0.15 mM Ca, or keratinocyte serum-free media (KSFM) from GIBCO containing 0.09 mM Ca). On day 7, when the cells were 80–90% confluent, they were trypsinized and plated in the serum-free medium for the various experiments.

Thymidine Assay $^3$H-Thymidine Incorporation and Keratinocyte Proliferation

The incorporation of $^3$H-thymidine by cultured keratinocytes was used as an assay of keratinocyte proliferation.

Thymidine is one of four deoxynucleosides which are the monomeric units of DNA, the universal library of genetic information in the animal kingdom. Prior to cell division of a somatic cell such as a keratinocyte, the complete genome of the cell undergoing cell division is replicated. This involves large scale DNA synthesis by the cell and enables both daughter cells to receive identical copies of the genetic material. When $^3$H-thymidine is included in the culture media of keratinocytes which are synthesizing DNA in preparation for cell division then the labelled nucleoside is incorporated into the newly synthesized DNA. The extent of incorporation of $^3$H-thymidine into a population of cells is proportional to the rate of DNA synthesis by this population of cells and therefore an indication of their cellular proliferation.

Keratinocytes (that were cultured as described above) were plated in 24 well plates at a density of 40,000 cells per well in 1 ml media. After incubation for four days or until the cells were 60-70% confluent, the media was changed. Test compounds were added (in triplicate) to the wells 24 hours after the media change, and four hours later 1 µCi $^3$H-Thymidine in 50 µl media was added per well. Cells were incubated for a further 24 hours. Media was removed from the cells, 10% ice cold trichloroacetic acid (TCA) added and plates were incubated on ice for 30 minutes. Cells were washed five times with 5% TCA and allowed to dissolve in 500 µl 0.1M NaOH for at least one hour (usually overnight). The preparations were neutralized with 0.1M HCl; 50 µl of the cell preparation was used to determine total protein content. Disintegrations per minute (DPM) from $^3$H labelling of DNA was determined by liquid scintillation counting of 900 µl of the cell preparation. Thymidine incorporation results were expressed as DPM/µg protein.

Transglutaminase Assay

Transglutaminase Assay and Keratinocyte Differentiation

During the process of terminal differentiation in the epidermis, a 15 nm thick layer of protein, known as the cornified envelope (CE) is formed on the inner surface of the cell periphery. The CE is composed of numerous distinct proteins which have been cross-linked together by the formation of $N^\epsilon$-($\gamma$-glutamyl) lysine isodipeptide bonds catalyzed by the action of at least two different transglutaminases (TGases) expressed in the epidermis. TGase I is expressed in abundance in the differentiated layers of the epidermis, especially the granular layer, but is absent in the undifferentiated basal epidermis. Thus TGase I is a useful marker of epidermal keratinocyte differentiation with high TGase I levels indicating a more differentiated state. An ELISA based TGase I assay, using a TGase I antibody, was used to assess the state of differentiation of the cultured keratinocytes in the examples that follow.

Keratinocytes (cultured as described above) were plated in 96 well plates at a density of 3,000 cells per well in 200 µl media. After incubation for four days the media was changed to media containing test compounds (six replicates per test). The cells were cultured for a further 72 hours after which time the media was aspirated and the plates stored at −70° C. Plates were removed from the freezer, and the cells washed with PBS. 100 µl sterile water was added and the cells were freeze fractured by freezing at −70° C. then thawing. The cells were incubated for one hour at room temperature (R/T) with PBS/3% BSA (wash buffer, bovine serum albumin), then rinsed with a fresh aliquot of wash buffer. Cells were incubated with 50 µl of primary antibodies monoclonal anti-human transglutaminase (IgG) obtained from Amersham (mouse) diluted 1:300 in wash buffer for one hour, 37° C. then rinsed two times with wash buffer. Cells were then incubated with 50 µl of secondary antibody (Feb fragment, peroxidase conjugated anti-mouse IgG obtained from Amersham) diluted 1:200 in wash buffer for one hour at 37° C., then rinsed two times with wash buffer. Cells were incubated with substrate solution (4 mg o-phenylene diamine and 3.3 µl 30% $H_2O_2$ in 10 ml 0.1M citrate buffer pH 5.0) for five minutes, R/T, in darkness (under aluminum foil). The reaction was stopped by the addition of 50 µl 4N $H_2SO_4$. The absorbance of samples was read at 492 nm in the plate reader. Out of the six replicates, four were treated with both antibodies, two were treated only with the secondary antibody (i.e., to determine background binding of enzyme conjugated Ab). TGase levels were determined by subtracting background from the readings from each treatment and determining mean ±s.d. for the replicates exposed to both Ab.

DNA Assay

The level of TGase-1 detected after treatment of the cells could be influenced by cell number, i.e., the greater the number of cells the greater the level of TGase-1 detected. The level of TGase-1 was normalized to DNA content of the cells in the same well thus eliminating variation due to differences in cell number. DNA quantitation is a particularly useful indicator of cell number, including keratinocyte cell number, because each cell has to all intents and purposes an identical genome and therefore an identical quantity of DNA. The total DNA content of a well of cells therefore is directly proportional to the cell number in that well. Quantitation of DNA was used to normalize the TGase data to cell number.

Keratinocytes were plated in 96 well plates at a density of 3,000 cells per well in 200 µl media. After incubation for four days the media was changed for media containing test compounds (6 replicates per test). The cells were cultured for a further 72 hours after which time the media was aspirated and the plates stored for at least 1.5 hours at −70° C. Plates were removed from the freezer, and the cells were fixed with cold 1:1 ethanol/acetone solution for 30 minutes. 100 µl/well of Hoechst dye (10 µg/ml final concentration) was added and this was incubated for 15 minutes, covered and then read in a fluorimeter (ex. 360 nm and em. 460 nm). The dye solution was removed and the wells were rinsed with PBS in preparation for the TGase assay.

EXAMPLE 1

Retinoic acid is more effective than retinol at altering keratinocyte differentiation state A. The effect on incorporation of $^3$H-thymidine µg soluble protein 24 hours after the addition of retinoic acid or retinol at various concentrations was examined. The results that were obtained are summarized in Table 1A.

TABLE 1A

EFFECT OF RETINOIC ACID (RA) AND RETINOL (ROH) ON KERATINOCYTE THYMIDINE INCORPORATION

| Treatment | mean Thymidine incorp./μg protein ± s.d (% control) | p value vs Control | p value vs $10^{-7}$M ROH | p value vs $10^{-8}$M ROH | p value vs $10^{-9}$M ROH |
|---|---|---|---|---|---|
| Control | 2094 ± 140 (100%) | — | 0.202 | 0.501 | 0.203 |
| $2.5 \times 10^{-7}$M RA | 2475 ± 116 (118%) | 0.005 | 0.032 | 0.004 | 0.002 |
| $2.5 \times 10^{-7}$M ROH | 2218 ± 73 (106%) | 0.202 | — | 0.021 | 0.005 |
| $2.5 \times 10^{-8}$M RA | 2686 ± 72 (128%) | 0.001 | 0.001 | 0.001 | 0.001 |
| $2.5 \times 10^{-8}$M ROH | 2034 ± 46 (97%) | 0.501 | 0.021 | — | 0.121 |
| $2.5 \times 10^{-9}$M RA | 2556 ± 80 (122%) | 0.001 | 0.006 | 0.001 | 0.001 |
| $2.5 \times 10^{-9}$M ROH | 1977 ± 19 (94%) | 0.203 | 0.005 | 0.121 | — | n = 3

All concentrations of retinoic acid tested, i.e., $2.5 \times 10^{-7}$M, $2.5 \times 10^{-8}$ and $2.5 \times 10^{-9}$M, significantly increased keratinocyte proliferation over both the ethanol control and each of the $2.5 \times 10^{-7}$M, $2.5 \times 10^{-8}$M and $2.5 \times 10^{-9}$M retinol treatments and they did so in a dose dependant manner. This is consistent with retinoic acid having a greater stimulatory effect on epithelial proliferation than retinol.

B. The effect on Transglutaminase levels after addition of retinoic acid and retinol was examined. The results that were obtained are summarized in Table 1B.

TABLE 1B

EFFECT OF RETINOIC ACID (RA) AND RETINOL (ROH) ON KERATINOCYTE TRANSGLUTAMINASE LEVEL

| Treatment | Mean TGase/DNA X $10^{-4}$ ± S.D. (% Control) | p value vs Control | p value vs $10^{-7}$ROH | p value vs $10^{-8}$ROH | p value vs $10^{-9}$ROH |
|---|---|---|---|---|---|
| Control | 2.44 ± 0.24 (100%) | — | 0.001 | 0.001 | 0.001 |
| $2.5 \times 10^{-7}$M RA | 0.16 ± 0.11 (7%) | 0.001 | 0.001 | 0.001 | 0.001 |
| $2.5 \times 10^{-7}$M ROH | 1.14 ± 0.22 (47%) | 0.001 | — | 0.001 | 0.001 |
| $2.5 \times 10^{-8}$M RA | 1.34 ± 0.40 (55%) | 0.001 | 0.00 | 0.001 | 0.001 |
| $2.5 \times 10^{-8}$M ROH | 1.89 ± 0.30 (77%) | 0.001 | 0.001 | — | 0.001 |
| $2.5 \times 10^{-9}$M RA | 1.87 ± 0.49 (77%) | 0.001 | 0.001 | 0.784 | 0.001 |
| $2.5 \times 10^{-9}$M ROH | 2.70 ± 0.59 (>100%) | 0.001 | 0.001 | 0.001 | — | n = 3

All concentrations of retinoic acid tested, i.e., $2.5 \times 10^{-7}$M, $2.5 \times 10^{-8}$M and $2.5 \times 10^{-9}$M decreased keratinocyte differentiation over both the ethanol control and each of the retinol treatments and did so to a significantly greater extent than each of the corresponding $2.5 \times 10^{-7}$M, $2.5 \times 10^{-8}$M and $2.5 \times 10^{-9}$M retinol treatments. The decrease in transglutaminase level was dose dependent for both retinoic acid and retinol. This is consistent with retinoic acid having a greater inhibitory effect on epithelial differentiation than retinol.

EXAMPLE 2

LINOLEOYL-DIETHANOLAMIDE (LINOLEOYL-DEA), BIFONAZOLE AND RETINOL ACT SYNERGISTICALLY TO ENHANCE KERATINOCYTE PROLIFERATION AND TO INHIBIT DIFFERENTIATION

A. The effect on incorporation of 3H-thymidine/μg soluble protein 24 hours after addition of the test compounds was examined and the combined results of three independent experiments were normalized to their respective ethanol controls. The results that were obtained are summarized in Table 2A.

TABLE 2A

EFFECT OF RETINOL, BIFONAZOLE AND LINOLEOYL-MEA
ON KERATINOCYTE THYMIDINE INCORPORATION

| Treatment | mean Thymidine incorp.µg protein ±s.d (% control) | p value vs. control | p value vs. $10^{-9}$ ROH | p value vs. $10^{-9}$ RA | p value vs. (*, @ ) |
|---|---|---|---|---|---|
| Control | 4368 ± 250 (100) | — | 0.105 | 0.008 | * = 0.103 @ = 0.0039 |
| $2.5 \times 10^{-9}$M RA | 5569 ± 248 (127%) | 0.008 | 0.002 | — | * = 0.158 @ = 0.085 |
| $2.5 \times 10^{-9}$M Retinal | 4856 ± 217 (111%) | 0.105 | — | 0.038 | * = 0.600 @ = 0.403 |
| $2.5 \times 10^{-9}$M ROH + $10^{-8}$M LADEA | 5027 ± 366 (115%) | 0.103 | 0.600 | 0.158 | — @ = 0.936 |
| $2.5 \times 10^{-9}$M ROH + $10^{-9}$M Bifonazole | 5052 ± 202 (116%) | 0.039 | 0.403 | 0.085 | * = 0.936 — |
| $2.5 \times 10^{-9}$M ROH + $10^{-8}$M LADEA + $10^{-9}$M Bifonazole | 5670 ± 68 (130%) | 0.011 | 0.029 | 0.142 | * = 0.153 @ = 0.048 | n = 3
* = p value vs $2.5 \times 10^{-9}$M ROH + $10^{-8}$M LADEA
@ = p value vs $2.5 \times 10^{-9}$M ROH + $10^{-9}$M Bifonazole $2.5 \times 10^{-9}$M retinoic acid significantly increased keratinocyte thymidine incorporation by 27% over the ethanol control and by 16% over the $2.5 \times 10^{-9}$M retinol treatment. Both $2.5 \times 10^{-9}$M retinol+$10^{-8}$M linoleamide-DEA and $2.5 \times 10^{-9}$M retinol+$10^{-9}$M bifonazole had a marginal stimulatory effect on keratinocyte proliferation over retinol on its own. However the combination of $2.5 \times 10^{-9}$M retinol+$10^{-8}$M linoleamide-DEA+$10^{-9}$M bifonazole significantly increased keratinocyte proliferation over both the ethanol and the $2.5 \times 10^{-8}$M retinol treatments by 30% and 19% respectively. The combination of $2.5 \times 10^{-9}$M retinol+$10^{-8}$M linoleamide-DEA+$10^{-9}$M bifonazole also increased keratinocyte proliferation over the $2.5 \times 10^{-9}$M retinol+$10^{-8}$M linoleamide-DEA and $2.5 \times 10^{-9}$M retinol+$10^{-9}$M bifonazole treatments. Fatty acid amides, bifonazole and retinol therefore, act synergistically to increase keratinocyte proliferation to levels which closely resemble the stimulatory effect of retinoic acid.

B. The effect on transglutaminase 1 (TG1) levels normalised to DNA content of the cells was examined in response to a 72 hour treatment with the test compounds and is shown in Table 2b.

levels. Retinol, fatty acid amides and bifonazole therefore act synergistically to repress keratinocyte differentiation in an analogous manner to the effect of retinoic acid.

EXAMPLE 3

LINOLEOYL-DEA, CLIMBAZOLE AND RETINOL SYNERGISTICALLY ENHANCED KERATINOCYTE PROLIFERATION AND INHIBITED DIFFERENTIATION

A. The effect of linoleoyl-DEA, climbazole and retinol on incorporation of $^3$H-thymidine was examined. The results that were obtained are summarized in Table 3A.

TABLE 2B

| Treatment | mean TGase/DNA × $10^{-4}$ ± s.d (% control) | p value vs Control | p value vs $10^{-8}$ ROH | p value vs $10^{-8}$ RA | p value vs $10^{-8}$ LAMAE + Bifon[1] |
|---|---|---|---|---|---|
| Control | 0.132 ± 0.027 (100%) | — | 0.001 | 0.001 | 0.010 |
| $2.5 \times 10^{-8}$M RA | 0.017 ± 0.010 (13%) | 0.001 | — | 0.001 | |
| $2.5 \times 10^{-8}$M Retinol | 0.111 ± 0.023 (84%) | 0.066 | — | 0.001 | 0.001 |
| $10^{-8}$M LA-MEA + $10^{-8}$ Bifonazole | 0.165 ± 0.026 (125%) | 0.010 | | | |
| $2.5 \times 10^{-8}$M ROH + $10^{-8}$M LA-MEA + $10^{-8}$M Bifonazole | 0.056 ± 0.047 (42%) | 0.001 | 0.010 | 0.037 | — | n = 6

$2.5 \times 10^{-8}$M retinoic acid was very effective at repressing keratinocyte TG1 levels i.e. to 13% of contol level. Neither $2.5 \times 10^{-8}$M retinol nor $10^{-8}$M LAMEA+$10^{-8}$M bifonazole had an inhibitory effect on the keratinocyte TG1 level. However $2.5 \times 10^{-8}$M retinol+$10^{-8}$M LAMEA+$10^{-8}$M bifonazole repressed keratinocyte TG1 to 42% of control

TABLE 3A

EFFECT OF RETINOL, CLIMBAZOLE AND LINOLEOYL-DEA ON KERATINOCYTE THYMIDINE INCORPORATION

| Treatment | mean Thymidine incorp/μg protein ± s.d (% control) | p value vs Control | p value vs $10^{-8}$ ROH | p value vs $10^{7}$ RA | p value vs (*, @ ) |
|---|---|---|---|---|---|
| Control | 3713 ± (100%) | — | 0.275 | 0.001 | * = 0.024 |
| 2.5 × $10^{7}$M RA | 4845 ± 95 (130%) | 0.001 | 0.001 | — | * = 0.006 |
|  |  |  |  |  | @ = 0.004 |
| 2.5 × $10^{8}$M Retinol | 3788 ± 57 (102%) | 0.275 | — | 0.001 | * = 0.043 |
|  |  |  |  |  | @ = 0.090 |
| 2.5 × $10^{8}$M ROH + $10^{8}$M LADEA | 4140 ± 160 (112%) | 0.024 | 0.043 | 0.006 | — |
|  |  |  |  |  | @ = 0.626 |
| 2.5 × $10^{8}$M ROH + $10^{9}$M Climbazole | 4056 ± 160 (109%) | 0.048 | 0.090 | 0.004 | * = 0.626 |
|  |  |  |  |  | — |
| 2.5 × $10^{8}$M ROH + $10^{8}$M LADEA + $10^{9}$M Climbazole | 4781 ± 196 (129%) | 0.002 | 0.002 | 0.697 | * = 0.023 |
|  |  |  |  |  | @ = 0.015 | n = 3
* = p value vs 2.5 × $10^{8}$M ROH + $10^{8}$M LADEA
@ = p value vs 2.5 × $10^{8}$M ROH + $10^{9}$ M Climbazole $2.5\times10^{-7}$M retinoic acid significantly increased keratinocyte thymidine incorporation by 30% over the ethanol control and by 28% over the 2.5×$10^{-8}$M retinol treatment. Both 2.5×$10^{-8}$M retinol+$10^{-8}$M linoleamide-DEA and 2.5× $10^{-8}$M retinol+$10^{-9}$M climbazole had a significant stimulatory effect on keratinocyte proliferation over the control and retinol on its own. However the combination of 2.5×$10^{-8}$M retinol+$10^{-8}$M linoleamide-DEA+$10^{-9}$M climbazole significantly increased keratinocyte proliferation over both the ethanol and the 2.5×$10^{-8}$M retinol treatments by 29% and 27% respectively. Most significantly the combination of 2.5×$10^{-8}$M retinol+$10^{-8}$M linoleamide-DEA+$10^{-9}$M climbazole also significantly increased keratinocyte proliferation over both the 2.5×$10^{-8}$M retinol+$10^{-8}$M linoleamide-DEA and 2.5×$10^{-8}$M retinol+$10^{-9}$M climbazole treatments by 17% and 20% respectively. Retinol, linoleamide-DEA and climbazole therefore, act synergistically to increase keratinocyte proliferation to levels which closely resemble the stimulatory effect of retinoic acid.

B. The effect on transglutaminase 1 (TG1) levels normalised to DNA content of the cells was examined in response to a 72 hour treatment with the test compounds and is shown in Table 3b.

more dilute 2.5×$10^{-9}$M retinoic acid was not as effective but still inhibited TG1 levels by 55%. 2.5×$10^{-9}$M retinol, 2.5× $10^{-9}$M retinol+$10^{-8}$M LADEA and 2.5×$10^{-9}$M retinol+$10^{-}$sM climbazole had no inhibitory effect on the keratinocyte TG1 level. However 2.5×$10^{-9}$M retinol+$10^{-8}$M LADEA+ $10^{-8}$M climbazole significantly repressed keratinocyte TG1 to 83% of control levels. This inhibition was significantly greater than the control, ROH alone, ROH+LADEA and ROH+climbazole indicating that the three ingredients, i.e., ROH, LADEA and climbazole act synergistically to inhibit keratinocyte TG1 levels. This effect was even greater when the climbazole concentration was increased by 10×, i.e., 2.5×$10^{-9}$M+$10^{-8}$M LADEA+$10^{-7}$M climbazole, which resulted in this combination inhibiting TG1 levels to 72% of control. Retinol, fatty acid amides and climbazole therefore act synergistically to repress keratinocyte differentiation in an analogous manner to the effect of retinoic acid.

EXAMPLE 4

CLOTRIMAZOLE, LINOLEAMIDE-MEA AND RETINOL SYNERGISTICALLY ENHANCED KERATINOCYTE PROLIFERATION

The effect on incorporation of $^3$H-thymidine/pg soluble protein 24 hours after addition of the test compounds was examined and the results are shown normalized to control in Table 4.

TABLE 3B

EFFECT OF RETINOL, CLIMBAZOLE AND LINOLEOYL-DEA ON KERATINOCYTETGASE LEVELS

| Treatment | mean TGase/DNA × $10^4$ ± s.d (% control) | p value vs Control | p value vs $10^9$OH | p value $10^9$ROH + LADEA | p value $10^8$OH + Climb' |
|---|---|---|---|---|---|
| Control | 1.52 ± 0.51 (100%) | — | 0.000 | 0.000 | 0.000 |
| 2.5 × $10^{7}$M RA | 0.44 ± 0.71 (29%) | 0.027 | 0.000 | 0.000 | 0.000 |
| 2.5 × $10^{9}$M RA | 0.84 ± 0.59 (55%) | 0.553 | 0.000 | 0.000 | 0.000 |
| 2.5 × $10^{9}$M Retinol | 1.96 ± 0.33 (129%) | 0.000 | — | 0.000 | 0.000 |
| 2.5 × $10^{9}$M ROH + $10^{8}$M LA-DEA | 1.59 ± 0.28 (105%) | 0.000 | 0.000 | — | 0.360 |
| 2.5 × $10^{9}$M ROH + $10^{8}$M Climbazole | 1.66 ± 0.42 (109%) | 0.000 | 0.000 | 0.360 | — |
| 2.5 × $10^{9}$M ROH + $10^{8}$LA-DEA + $10^{8}$M Climbazole | 1.27 ± 0.51 (83%) | 0.000 | 0.000 | 0.000 | 0.000 |
| 2.5 × $10^{9}$M ROH +$10^{8}$M LA-DEA + $10^{7}$M Climbazole | 1.10 = 0.40 (72%) | 0.009 | 0.000 | 0.000 | 0.000 | n = 6

$2.5\times10^{-7}$M retinoic acid was very effective at repressing keratinocyte TG1 levels (to 29%) of contol level whereas the

TABLE 4

EFFECT OF RETINOL, LINOLEAMIDE-MEA AND CLOTRIMAZOLE ON KERATINOCYTE THYMIDINE INCORPORATION

| Treatment | mean Thymidine incorp/μg protein ± s.d (% control) | p value vs Control | p value vs $10^8$ ROH | p value vs $10^7$ RA | p value vs (*, @ ) |
|---|---|---|---|---|---|
| Control | 1.00 ± 0.11 (100%) | — | 0.041 | 0.001 | * = 0.152<br>@ = 0.099 |
| 2.5 × $10^9$M RA | 1.28 ± 0.09 (128%) | 0.001 | 0.002 | — | * = 0.001<br>@ = 0.041 |
| 2.5 × $10^9$M Retinol | 1.13 ± 0.09 (113%) | 0.041 | — | 0.002 | * = 0.176<br>@ = 0.853 |
| 2.5 × $10^9$M ROH + $10^8$M LAMEA | 1.08 ± 0.09(108%) | 0.152 | 0.176 | 0.001 | —<br>@ = 0.587 |
| 2.5 × $10^9$M ROH + $10^{8M}$ Clotrimazole | 1.12 ± 0.12 (112%) | 0.099 | 0.853 | 0.041 | * = 0.587<br>— |
| 2.5 × $10^9$M ROH + $10^8$M LAMEA + $10^8$M Clotrimazole | 1.29 ± 0.09 (129%) | 0.001 | 0.003 | 0.572 | * = 0.001<br>@ = 0.039 | n = 3
* = p value vs 2.5 × $10^8$M ROH + $10^8$M LAMEA
@ = p value vs 2.5 × $10^8$M ROH + $10^8$M Clotrimazole $2.5 \times 10^{-9}$M retinoic acid significantly increased keratinocyte thymidine incorporation by 28% over the ethanol control and by 15% over the $2.5 \times 10^{-9}$M retinol treatment. Both $2.5 \times 10^{-9}$M retinol+$10^{-8}$M linoleamide-MEA and $2.5 \times 10^{-9}$M retinol+$10^{-8}$M clotrimazole had a stimulatory effect on keratinocyte proliferation over the control but this effect was no greater than retinol on its own. However the combination of $2.5 \times 10^{-9}$M retinol+$10^{-8}$M linoleamide-MEA+$10^{-8}$M clotrimazole significantly increased keratinocyte proliferation over both the ethanol control and the $2.5 \times 10^{-9}$M retinol treatment by 29% and 16% respectively. Most unexpectedly the combination of $2.5 \times 10^{-9}$M retinol+$10^{-8}$M linoleamide-MEA+$10^{-8}$M clotrimazole also significantly increased keratinocyte proliferation over both the $2.5 \times 10^{-9}$M retinol+$10^{-8}$M linoleamide-MEA and $2.5 \times 10^{-9}$M retinol+$10^{-8}$M clotrimazole treatments by 21% and 17% respectively. Retinol, linoleamide-MEA and clotrimazole therefore, act synergistically to increase keratinocyte proliferation to levels which closely resemble the stimulatory effect of retinoic acid.

Examples 1-4 demonstrate that retinoic acid, in a dose dependant manner, increased thymidine incorporation and decreased transglutaminase I levels in skin keratinocytes. In other words retinoic acid increased keratinocyte proliferation and decreased keratinocyte differentiation. In Examples 1-4, retinoic acid was used as positive control and reference compound against which the other compounds under analysis were compared. Retinol was significantly less effective than retinoic acid at inhibiting keratinocyte differentiation and completely ineffective at increasing keratinocyte proliferation.

The unexpected results of Examples 1-4, however, were that the effect of retinol on cultured keratinocytes can be enhanced to levels approaching those of retinoic acid by combining retinol or retinyl ester with a fatty acid amide and an azole, although an azole and a fatty acid amide each exerts little or no benefit on its own. The results documented above demonstrate that fatty acid amides in combination with azoles act synergistically with retinol or retinyl ester, both to increase keratinocyte proliferation and to decrease keratinocyte differentiation, mimicking the effect of retinoic acid.

The unexpected result of this study was that the effect of retinol on cultured keratinocytes can be enhanced to levels approaching those of retinoic acid by combining retinol with a fatty acid amide and an azole. This effect was not only greater than the effect of either retinol+fatty acid amide or of retinol+azole but the three ingredients acted in synergy with each other to promote a retinoic acid type response.

The results documented above demonstrate that fatty acid amides and azoles act synergistically with retinol both to increase keratinocyte proliferation and decrease keratinocyte differentiation, mimicking the effect of retinoic acid.

EXAMPLE 6

This example illustrates a high internal phase water-in-oil emulsion incorporating the inventive composition.

|  | % w/w |
|---|---|
| Retinol | 0.5 |
| Miconazole | 1 |
| Linoleoyl-diethanolamide | 5 |
| Fully hydrogenated coconut oil | 3.9 |
| Brij 92* | 5 |
| Bentone 38 | 0.5 |
| $MgSO_4 7H_2O$ | 0.3 |
| Butylated hydroxy toluene | 0.01 |
| Perfume | qs |
| Water | to 100 |

*Brij 92 is polyoxyethylene (2) oleyl ether

EXAMPLE 7

This example illustrates an oil-in-water cream incorporating the inventive composition.

|  | % w/w |
|---|---|
| Retinol | 0.15 |
| Clotrimazole | 2 |
| Cocoyl diethanolamide | 1 |
| Mineral oil | 4 |
| Brij 56* | 4 |
| Alfol 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

-continued

|  | % w/w |
|---|---|
| *Brij 56 is cetyl alcohol POE (10) | |
| Alfol 16RD is cetyl alcohol | |

EXAMPLE 8

This example illustrates an alcoholic lotion incorporating the composition according to the invention.

|  | % w/w |
|---|---|
| Retinyl palmitate | 0.15 |
| Linoleoyl monoethanolamide | 0.1 |
| Climobazole | 1 |
| Ethanol | 40 |
| Perfume | qs |
| Butylated hydroxy toluene | 0.01 |
| Water | to 100 |

EXAMPLE 9

This example illustrates another alcoholic lotion containing the inventive composition.

|  | % w/w |
|---|---|
| Retinol | 0.15 |
| Palmitoyl-monoethanolamide | 0.1 |
| Climbazole | 2 |
| Ethanol | 40 |
| Antioxidant | 0.1 |
| Perfume | qs |
| Water | to 100 |

EXAMPLE 10

This example illustrates a suncare cream incorporating the composition of the invention:

|  | % w/w |
|---|---|
| Retinol | 0.01 |
| Linoleoyl monoethanolamide | 0.1 |
| Climbazole | 0.1 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 11

This example illustrates a non-aqueous skin care composition incorporating the inventive combination.

|  | % w/w |
|---|---|
| Retinol palmitate | 0.15 |
| Linoleoyl diethanolamide | 1 |
| Miconazole | 0.1 |
| Silicone gum SE-30[1] | 10 |
| Silicone fluid 345[2] | 20 |
| Silicone fluid 344[3] | 55.79 |
| Squalene | 10 |
| Linoleic acid | 0.01 |
| Cholesterol | 0.03 |
| 2-hydroxy-n-octanoic acid | 0.7 |
| Vitamin E linoleate | 0.5 |
| Herbal oil | 0.5 |
| Ethanol | 2 |

[1] A dimethyl silicone polymer having a molecular weight of at least 50,000 and a viscosity of at least 10,000 centistokes at 25° C., available from GEC
[2] Dimethyl siloxane cyclic pentamer, available from Dow Corning Corp.
[3] Dimethyl siloxane tetramer, available from Dow Corning Corp.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin conditioning composition comprising (a) from about 0.001% to about 10% of a compound selected from the group consisting of retinol;

(b) from about 0.0001% to about 50% of an azole selected from the group consisting of climbazole, miconazole, bifonazole, clotrimazole, econazole;

(c) from about 0.0001% to about 50% of a fatty acid amide selected from the group consisting of linoleoyl monoethanolamide, linoleoyl diethanolamide, palmitoyl monoethanolamide, palmitoyl diethanolamide, cocoyl monoethanolamide, cocoyl diethanolamide, and mixtures thereof; and (d) a cosmetically acceptable vehicle.

2. A method of treating a skin condition selected from the group consisting of dry skin, photodamaged skin, appearance of wrinkles, age spots and aged skin, the method comprising applying to the skin the composition of claim 1.

* * * * *